US009220836B2

(12) United States Patent
Salgia et al.

(10) Patent No.: US 9,220,836 B2
(45) Date of Patent: Dec. 29, 2015

(54) PORTABLE PUMP FOR INTRAVENOUS FLUIDS

(71) Applicant: LifeMedix Statfusion, LLC, Akron, OH (US)

(72) Inventors: Anup T. Salgia, Akron, OH (US); William D. Kolosi, Northfield, OH (US)

(73) Assignee: LifeMedix Statfusion, LLC, Akron, OH (US)

( * ) Notice: Subject to any disclaimer, the term of this patent is extended or adjusted under 35 U.S.C. 154(b) by 378 days.

(21) Appl. No.: 13/667,606

(22) Filed: Nov. 2, 2012

(65) Prior Publication Data

US 2013/0060195 A1    Mar. 7, 2013

Related U.S. Application Data

(63) Continuation of application No. 12/748,700, filed on Mar. 29, 2010, now Pat. No. 8,337,466.

(60) Provisional application No. 61/164,763, filed on Mar. 30, 2009.

(51) Int. Cl.
*A61M 1/00* (2006.01)
*A61M 5/142* (2006.01)

(52) U.S. Cl.
CPC ......... *A61M 5/1424* (2013.01); *A61M 5/14224* (2013.01)

(58) Field of Classification Search
CPC ................. A61M 2005/14268; A61M 5/1413; A61M 1/16; A61M 5/1408; A61M 5/1424; A61M 5/148; A61M 5/1483; A61M 5/1409
See application file for complete search history.

(56) References Cited

U.S. PATENT DOCUMENTS

| 4,410,322 A | 10/1983 | Archibald |
| 4,472,116 A | 9/1984 | Wenstrup |
| 4,538,918 A | 9/1985 | Mittleman |

(Continued)

FOREIGN PATENT DOCUMENTS

| CN | 201001863 | 1/2008 |
| CN | 101224315 | 7/2008 |

OTHER PUBLICATIONS

International Search Report and Written Opinion of the International Searching Authority in Corresponding PCT Application No. PCT/US2010/029185 filed Mar. 30, 2010; Authorized Officer Blaine Copenheaver; May 24, 2010.

(Continued)

*Primary Examiner* — Emily Schmidt
(74) *Attorney, Agent, or Firm* — Squire Patton Boggs (US) LLP

(57) ABSTRACT

A device includes at least one housing, a first input line operatively connected to a fluid source that is external to the at least one housing, and a second input line operatively connected to the fluid source. The device further includes a first fluid reservoir operatively connected to the first input line and a second fluid reservoir operatively connected to the second input line. An output line is operatively connected to the first fluid reservoir and the second fluid reservoir. An actuator is configured to facilitate a flow of fluid from the fluid source, through the first input line and second input line, and through the first fluid reservoir and second fluid reservoir. Each of the first and second input lines remains operatively connected to the fluid source during operation of the actuator.

16 Claims, 16 Drawing Sheets

(56) References Cited

U.S. PATENT DOCUMENTS

| | | | |
|---|---|---|---|
| 4,710,166 A * | 12/1987 | Thompson et al. | 604/81 |
| 4,747,832 A | 5/1988 | Buffet | |
| 4,776,840 A | 10/1988 | Freitas et al. | |
| 5,336,189 A | 8/1994 | Sealfon | |
| 5,348,539 A | 9/1994 | Herskowitz | |
| 5,498,246 A | 3/1996 | Deutchman et al. | |
| 5,554,123 A | 9/1996 | Herskowitz | |
| D398,053 S | 9/1998 | Sealfon | |
| 5,951,517 A | 9/1999 | Lampropoulos et al. | |
| 6,171,234 B1 | 1/2001 | White et al. | |
| 6,500,156 B1 | 12/2002 | Stansbury | |
| 6,551,277 B1 | 4/2003 | Ford | |
| 7,018,361 B2 | 3/2006 | Gillespie, Jr. et al. | |
| 7,059,840 B2 | 6/2006 | Corwin et al. | |
| 7,182,750 B2 | 2/2007 | Lampropoulos et al. | |
| 7,311,691 B2 | 12/2007 | Cartledge et al. | |
| 7,326,186 B2 | 2/2008 | Trombley, III et al. | |
| 7,337,922 B2 | 3/2008 | Rake et al. | |
| 7,500,962 B2 | 3/2009 | Childers et al. | |
| 7,503,903 B2 | 3/2009 | Carlisle et al. | |
| 2003/0190246 A1 | 10/2003 | Corwin et al. | |
| 2004/0073175 A1 | 4/2004 | Jacobson et al. | |
| 2004/0242996 A1 | 12/2004 | Trombley, III et al. | |
| 2005/0171512 A1 | 8/2005 | Flaherty | |
| 2005/0192529 A1 | 9/2005 | Butterfield et al. | |
| 2007/0010798 A1 | 1/2007 | Stoller et al. | |
| 2009/0163860 A1 * | 6/2009 | Patrick et al. | 604/83 |
| 2010/0292651 A1 | 11/2010 | Yodfat et al. | |
| 2011/0144586 A1 | 6/2011 | Michaud et al. | |
| 2012/0209197 A1 | 8/2012 | Lanigan et al. | |

OTHER PUBLICATIONS

Notice of Allowance and Fee(s) Due in Corresponding U.S. Appl. No. 12/748,700, filed Mar. 29, 2010; Oct. 1, 2012.

Office Action in Corresponding U.S. Appl. No. 12/748,700, filed Mar. 29, 2010; Jun. 4, 2012.

Office Action in Corresponding U.S. Appl. No. 12/748,700, filed Mar. 29, 2010; Feb. 23, 2012.

Office Action in Corresponding U.S. Appl. No. 12/748,700, filed Mar. 29, 2010; Nov. 23, 2011.

Office Action; Corresponding Chinese Patent Application No. 201410019075.4; Mar. 11, 2015.

Office Action; Corresponding U.S. Appl. No. 13/476,411, filed May 21, 2012; dated May 28, 2015.

* cited by examiner

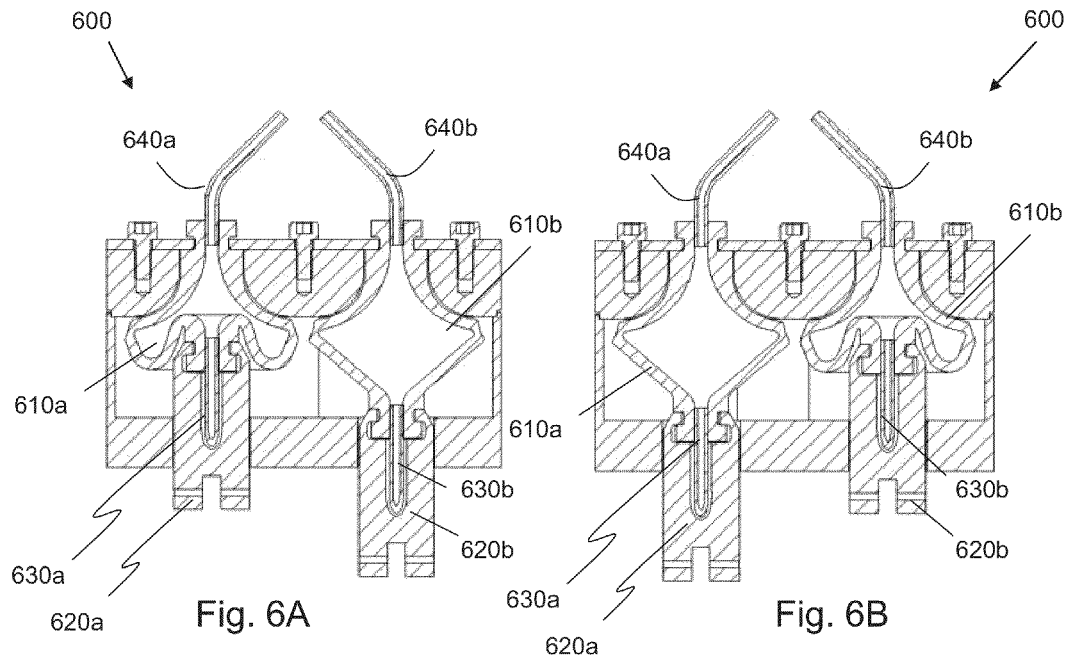
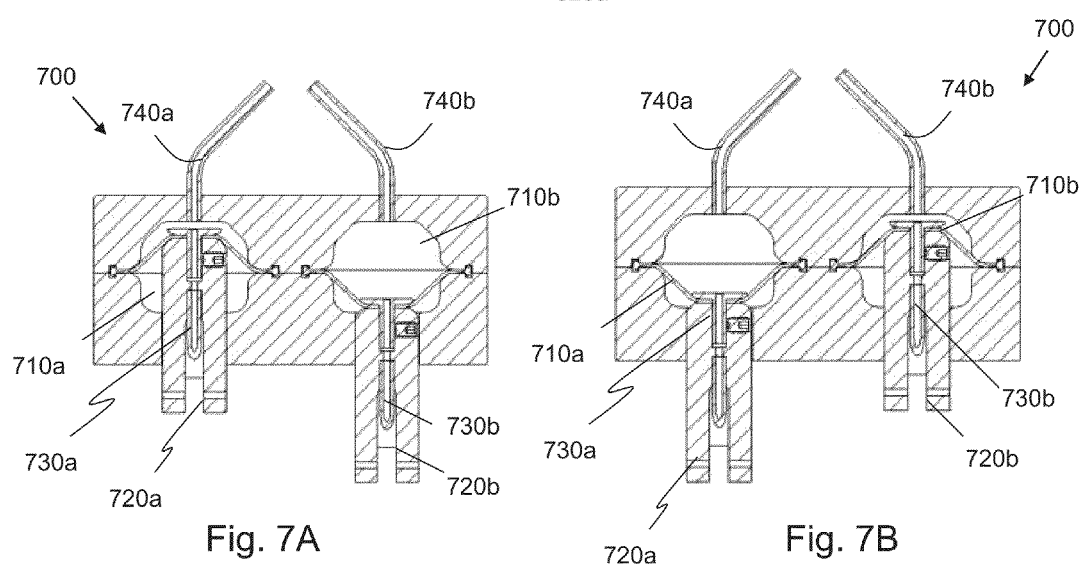

PORTABLE PUMP FOR INTRAVENOUS FLUIDS

CROSS REFERENCE TO RELATED APPLICATIONS

This application is a continuation of U.S. patent application Ser. No. 12/748,700 filed on Mar. 29, 2010, which claims the benefit of priority of U.S. Provisional Application No. 61/164,763, filed on Mar. 30, 2009. Both applications are incorporated herein, in their entirety.

FIELD OF INVENTION

The present application relates to devices for infusing intravenous fluids. More particularly, the present application relates to a portable pump for infusing intravenous fluids into a subject.

BACKGROUND

In the medical and veterinary setting, the need may arise to rapidly infuse intravenous fluid into a subject. Saline and lactated ringers are examples of commonly used intravenous fluids. Such fluids may be used to maintain or elevate blood pressure and promote adequate perfusion. In the shock-trauma setting or in septic shock, fluid resuscitation is often first-line therapy to maintain or improve blood pressure.

Currently, a first responder, such as emergency medical technicians or military field medics, are known to administer intravenous fluids with a gravity drip, having a fluid bag, a fluid line, and an needle or intravenous catheter. When the needle or intravenous catheter is inserted into a subject, gravity causes the fluid to flow from the fluid bag, through the fluid line and needle, and into the subject. To increase the speed at which intravenous fluids are infused into the subject, the technician may apply pressure on the bag. Pressure may be applied by hand, by employing a blood pressure cuff, or other external pneumatic pressure device on the fluid bag itself.

Additionally, intraosseous (I.O.) lines have gained wider use in pediatric subjects, as well as adult subjects. Intraosseous infusion is a process of injection directly into the marrow of a subject's bone. Intraosseous lines often have a relatively slow rate of infusion.

There also exist several types of electronic pumps that infuse intravenous fluids. Such electronic pumps are often very costly and complex, and may require special training to operate. Further, such pumps may be delicate and not suited for field use. A first responder company will require several of these, adding to cost. Lastly, electronic pumps require a power source, such as a battery or wall socket, and may not necessarily be friendly to the environment.

SUMMARY OF THE INVENTION

In one embodiment, an intravenous pump includes an actuator housing including a first facilitating member and a second facilitating member. The intravenous pump also includes a reservoir housing removably attached to the actuator housing. The reservoir housing includes a first fluid input line, having a first end and a second end. The first end is configured to be operatively connected to a fluid source that is external to the actuator housing and external to the reservoir housing. The reservoir housing further includes a first fluid reservoir operatively connected to the second end of the first fluid input line. The reservoir housing also has a second fluid input line, with a first end and a second end. The first end is configured to be operatively connected to the fluid source. The reservoir housing further includes a second fluid reservoir operatively connected to the second end of the second fluid input line and at least one fluid output line operatively connected to the first fluid reservoir and the second fluid reservoir. The first facilitating member is configured to facilitate flow of a fluid from the fluid source through the first fluid reservoir. The second facilitating member is configured to facilitate flow of a fluid from the fluid source through the second fluid reservoir. The first end of the first fluid input line and the first end of the second fluid input line each remain operatively connected to the fluid source during actuation of the first facilitating member and the second facilitating member.

In another embodiment, a device includes at least one housing, a first input line operatively connected to a fluid source that is external to the at least one housing, and a second input line operatively connected to the fluid source. The device further includes a first fluid reservoir operatively connected to the first input line and a second fluid reservoir operatively connected to the second input line. An output line is operatively connected to the first fluid reservoir and the second fluid reservoir. An actuator is configured to facilitate a flow of fluid from the fluid source, through the first input line and second input line, and through the first fluid reservoir and second fluid reservoir. Each of the first and second input lines remains operatively connected to the fluid source during operation of the actuator.

In yet another embodiment, an intravenous fluid pumping kit includes a fluid bag, a fluid line, and a pump. The pump includes a housing, and a first fluid reservoir having a first fluid input operatively connected to the fluid bag and a fluid output. The pump also includes a second fluid reservoir having a second fluid input line operatively connected to the fluid bag. The second fluid reservoir is further connected to the fluid output. The pump further includes a facilitator configured to facilitate flow of fluid through the first and second fluid reservoirs from the fluid bag, through the first and second fluid inputs, and to the fluid output. The fluid bag is external to the housing.

BRIEF DESCRIPTION OF THE DRAWINGS

In the accompanying drawings, structures are illustrated that, together with the detailed description provided below, describe exemplary embodiments of the claimed invention.

In the drawings and description that follows, like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

FIGS. 6A and 6B are cross-sections of one embodiment of a reservoir housing having a pair of asymmetric diaphragm pumps;

FIGS. 7A and 7B are cross-sections of one embodiment of a reservoir housing having a pair of symmetric diaphragm pumps;

DETAILED DESCRIPTION

Multiple embodiment of intravenous pumps are shown and described herein. It should be understood that the disclosed pumps may be employed to pump any known intravenous fluids, including, without limitation, saline, lactated ringers, colloid solution, platelets, and blood. Further, the use of the disclosed pumps is not limited to the intravenous application of fluids. It should be understood that the pumps may be used, for example, for wound irrigation or other cleaning or sterilization purposes. For such uses, the pumps may be used with water, alcohol, or other sterilants.

Figure 1:
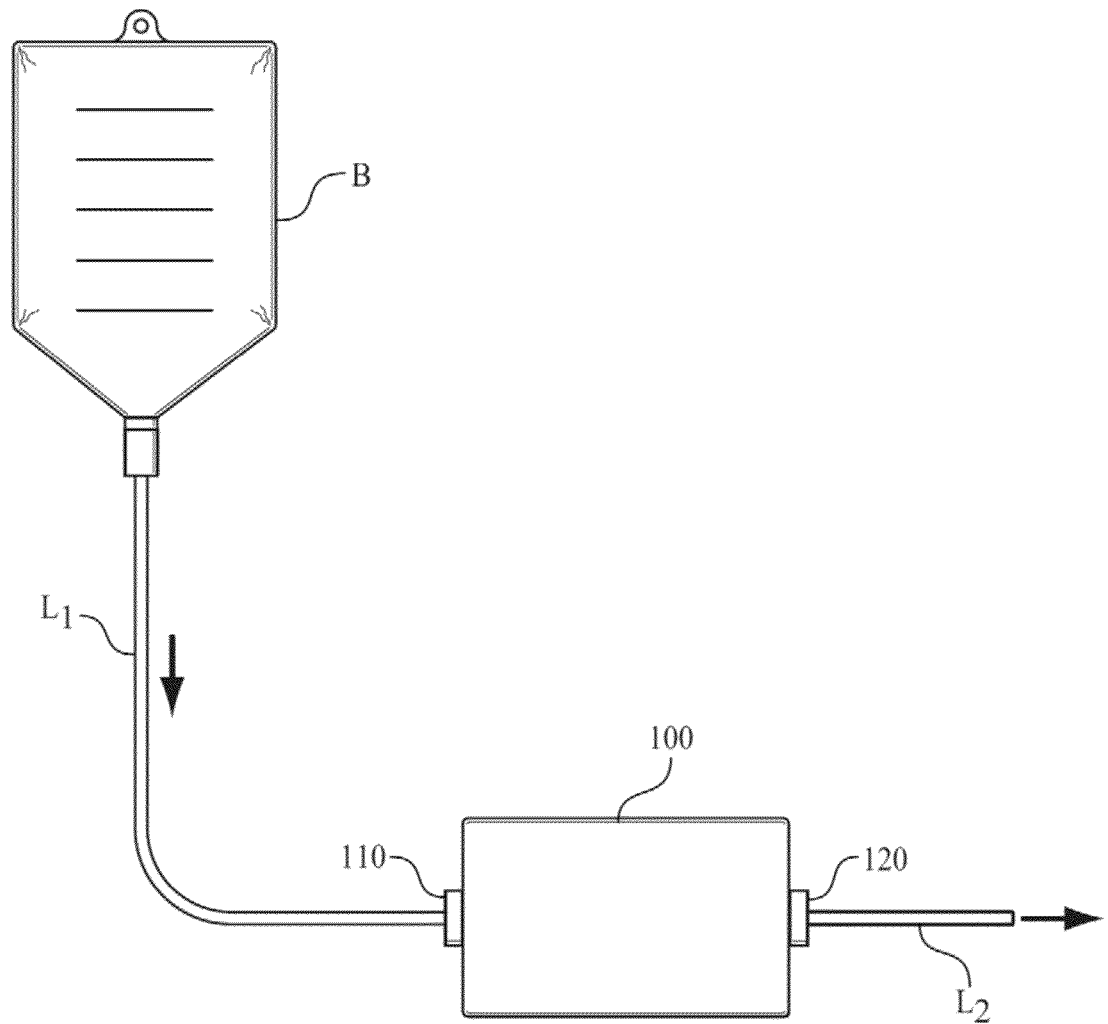
FIG. 1 is a schematic drawing of a manual intravenous pump in combination with a fluid bag and a fluid line.

FIG. 1 is a schematic drawing of a manual intravenous pump 100 in combination with a fluid bag B and a fluid line L. In the illustrated embodiment, the fluid line L includes a first line $L_1$ and a second line $L_2$. The first fluid line $L_1$ is connected to an output of the fluid bag B and an input 110 of the manual intravenous pump 100. The first fluid line L leads to an internal fluid reservoir (not shown) in the manual intravenous pump 100. The manual intravenous pump 100 further includes one or more mechanisms (not shown) to facilitate the flow of fluid through the internal fluid reservoir. In one embodiment, the input 110 of the manual intravenous pump 100 is a one-way valve. In alternative embodiments, the input may be a 2-way valve, or an adjustable, bi-directional valve.

The second fluid line $L_2$ is connected to an output 120 of the manual intravenous pump 100 and leads to a subject, usually by a needle or intravenous catheter. Alternatively, the manual intravenous pump 100 may employ central line catheters and interosseous lines. In one embodiment, the output 120 is also a one-way valve. One-way valves allows the fluid only to flow from the fluid bag B, to the subject, and not in a reverse direction. In alternative embodiments, however, the output may be a 2-way valve, or an adjustable, bi-directional valve.

The manual intravenous pump 100 may be used in-line (i.e., in series) as described above. Alternatively, the manual intravenous pump 100 may also be used in a bypass-type configuration (i.e., in parallel) to allow a gravity drip to continue.

The manual intravenous pump 100 further includes a manually operable actuator (not shown), configured to force fluid from the input 110 of the manual intravenous pump 100 to the output 120. Various types of manually operable actuators may be employed. Exemplary manual operable actuators are discussed below. These examples are not intended to be limiting.

Figure 2:
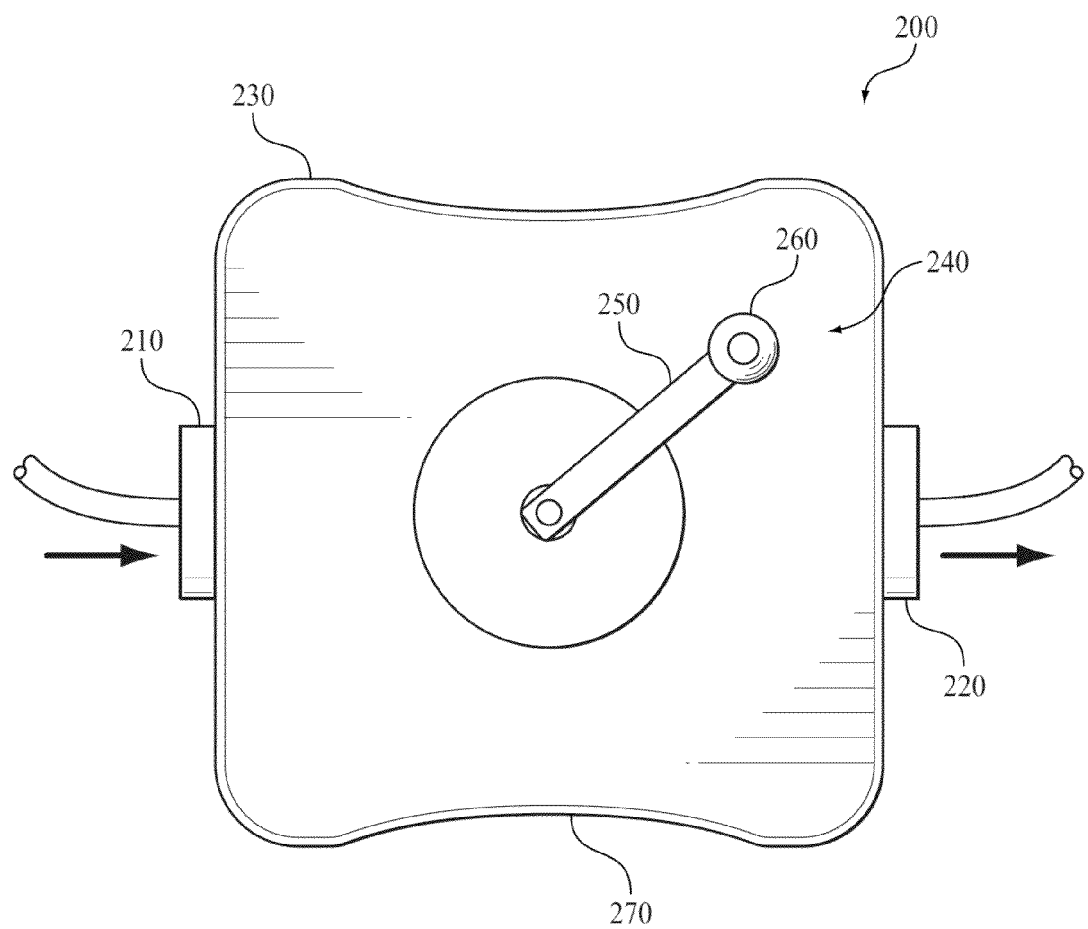
FIG. 2 is a top view of one embodiment of a manual intravenous pump having a crank.

FIG. 2 illustrates a top view of one embodiment of a manual intravenous pump 200 having an input 210, an output 220, and a body 230. In this embodiment, the manually operable actuator is a crank 240. This type of manual intravenous pump may be referred to as a "crank design," "crank pump," or "hand crank." The crank 240 includes a lever arm 250 rotatably connected to the body 230 of the manual intravenous pump 200. In the illustrated embodiment, the crank 240 further includes a handle 260 connected to the lever arm 250. The handle 260 may be rotatably or fixedly connected to the lever arm 250. In one embodiment, the crank 240 is a single, unitary piece including a lever arm portion and handle portion.

In the illustrated embodiment, the manual intravenous pump 200 further includes a pair of handles 270. The handles 270 may be solid or flexible. The handles may be ergonomically shaped for the comfort of the user. Further, the handles may be located in an ergonomic position for the comfort of the user. In an alternative embodiment (not shown), the manual intravenous pump includes three or more handles. In another alternative embodiment (not shown), the manual intravenous pump includes a single handle. In yet another alternative embodiment (not shown), the manual intravenous pump does not include any handles, and could have contours that are designed for ergonomic handling.

With continued reference to FIG. 2, the body 230 of the manual intravenous pump 200 has an approximately cubic shape, with rounded edges. However, it should be understood that this shape is merely exemplary, and any shape may be employed. In one embodiment, the body may have an ergonomic shape.

Although FIG. 2 is described as a top view, it should be understood that the crank 260 and optional handles 270 may be located on any surface of the manual intravenous pump 200, such as a side or bottom surface. Further, in one embodiment, the manual intravenous pump 200 is designed to be positioned in multiple orientations, so that the operator may position the device in a comfortable orientation for operation.

The manual intravenous pump 200 may be constructed of various materials. Exemplary materials include polymeric materials and metal materials. Exemplary metal materials include, without limitation, steel, nickel aluminum, copper, iron, and other metals and alloys. Exemplary polymeric materials include, without limitation, EPDM Rubber, latex, polypropylene, polyethylene, and blends of the same. In one embodiment, where the manual intravenous pump is configured for field use (i.e., in an ambulance, or at an accident site), the device may be constructed of materials that are lightweight and durable. Of course, such materials may also be suitable for a device configured for clinical use. In one embodiment, the casing 230, the crank 240, and the handles 270 are all constructed of substantially the same material. In an alternative embodiment, one or more of these components are constructed of different materials.

Figure 3:
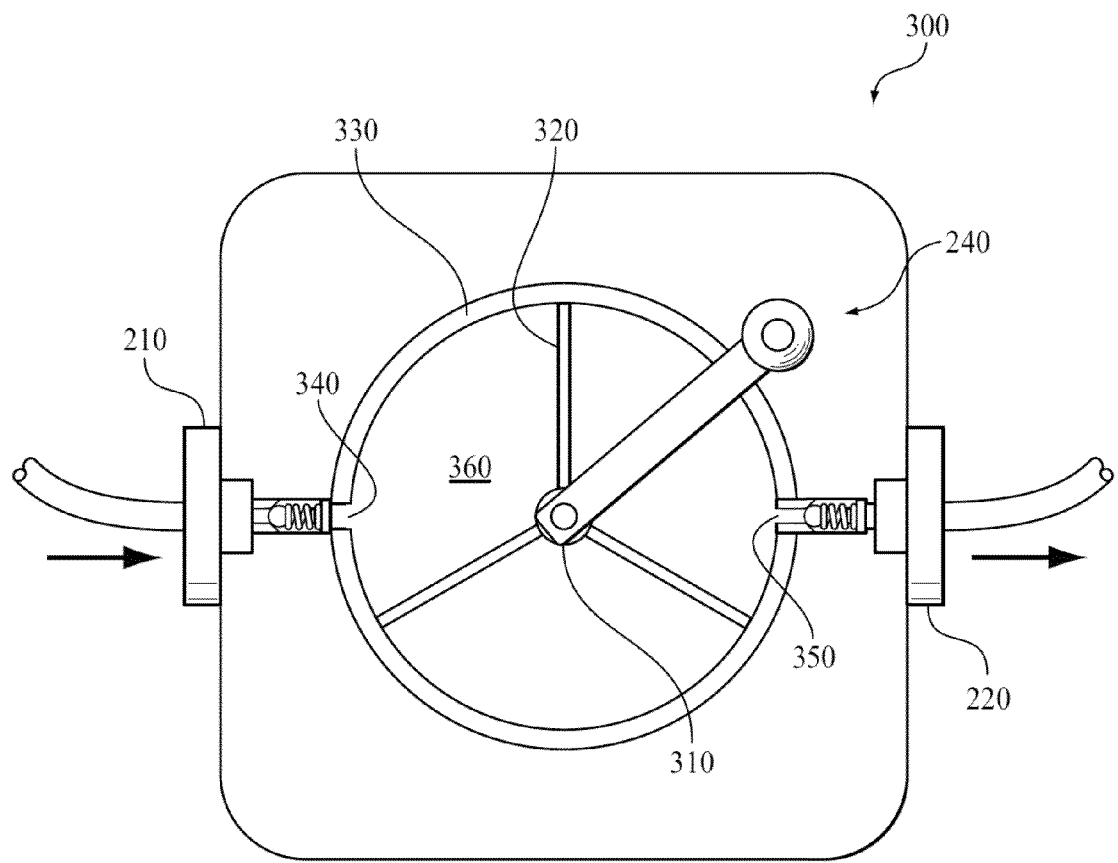
FIG. 3 is a top cutaway view of one embodiment of a manual intravenous pump having a crank and rotary chambers.

FIG. 3 is a top cutaway view of one embodiment of a manual intravenous pump 300. The illustrated embodiment is one example of the internal components of the crank design of a manual intravenous pump 200 shown in FIG. 2.

In the illustrated embodiment, the crank 240 is connected to a rod 310 having a plurality of partitions 320 extending therefrom. The rod 310 and partitions 320 are positioned inside a cylinder 330 that defines an internal fluid reservoir of the manual intravenous pump 300. The cylinder 330 has a first opening 340 in fluid communication with the input 210 of the manual intravenous pump 300 and a second opening 350 in fluid communication with the output 220 of the manual intravenous pump 300. The rod 310 and partitions 320 form a plurality of rotary chambers 360 in the cylinder 330. In the illustrated embodiment, the rod 310 includes three partitions 320 extending therefrom, which form three rotary chambers 360 in the cylinder 330. However, it should be understood that any number of partitions may be employed, including a single partition.

In addition to the components shown, various gear configurations may be employed to create a mechanical advantage and/or cause the rod 310 and partitions 320 to rotate at a rate different from the rate at which the crank 240 is turned.

Various materials may be used to construct the rod 310, partitions 320, and cylinder 330. Exemplary materials include polymeric materials and metal materials. In one embodiment, the rod 310, partitions 320, and cylinder 330 are constructed of polymeric materials that resist corrosion after prolonged exposure to saline solutions and other commonly used intravenous fluids. In one embodiment, the rod 310, partitions 320, and cylinder 330 are all constructed of substantially the same material. In an alternative embodiment, one or more of these components are constructed of different materials.

With continued reference to FIG. 3, the partitions 320 extend from the rod 310 to an inner surface of the cylinder 330. In one embodiment, at least the ends of the partitions are constructed of rubber, or another pliable, non-porous material, to form a seal. It should be understood, however, that various other materials may be employed. In an alternative embodiment, the partitions 320 do not extend to the inner surface of the cylinder 330.

In operation, the input 210 of the manual intravenous pump 300 is connected to a first fluid line leading to a fluid bag, and the output 220 is connected to a fluid line leading to a subject. In one embodiment, both the input 210 and the output 220 are one-way valves. In one embodiment, when a fluid line is connected to the input 210, fluid immediately begins to flow from the fluid bag, through the fluid line and input 210, and into the first of the plurality of chambers 360. In an alternative embodiment, fluid will not begin to flow until the input 210 is opened (e.g., by turning or pressing a valve).

Once the fluid lines have been connected to the fluid bag, the manual intravenous pump 300, and the subject, and the fluid has begun to flow, an operator may turn the crank 240 of the manual intravenous pump 300. As the crank 240 is turned, the partitions 320 rotate at a corresponding speed and force the fluid from the first opening 340 of the cylinder 330 towards the second opening 350. In the illustrated embodiment, the crank 240 may be turned in either a clockwise or a counter-clockwise direction. Turning the crank 240 at a faster rate may increase the rate at which fluid flows through the output 350 and to a subject, while turning the crank 240 at a slower rate may decrease the rate at which fluid flows through the output 220 and to a subject. The operator may control the speed at which the crank 220 is turned, according to perceived need.

Figure 4:
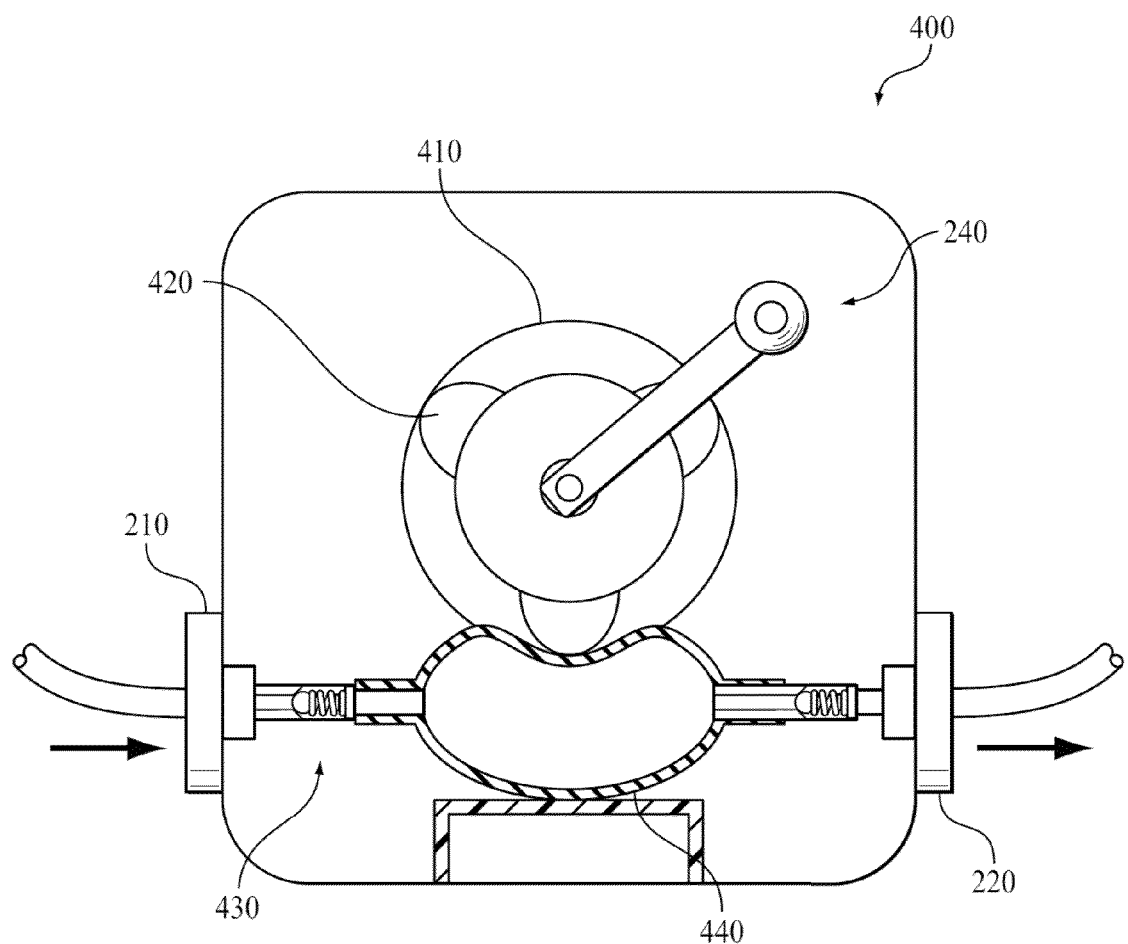
FIG. 4 is a top cutaway view of an alternative embodiment of a manual intravenous pump having a crank and a bulb.

FIG. 4 is a top cutaway view of an alternative embodiment of a manual intravenous pump 400. The illustrated embodiment is another example of the internal components of the crank design of a manual intravenous pump 200 shown in FIG. 2.

In the illustrated embodiment, the crank 240 is connected to a disc 410 having a plurality of spaced apart, projections 420 extending therefrom. The disc 410 may be substantially circular or eccentric. The manual intravenous pump 400 further includes an internal fluid line 430 having a bulb 440 that defines an internal fluid reservoir of the manual intravenous pump 400. The internal fluid line 430 is in fluid communication with both the input 210 and the output 220 of the manual intravenous pump 400. The disc 410 and projections 420 are positioned adjacent the bulb 440, such that the projections 420 contact and deform the bulb 440 when the disc 410 is rotated. In the illustrated embodiment, the disc 410 includes three projections 420 extending therefrom. However, it should be understood that any number of projections may be employed, including a single projection.

In the illustrated embodiment, the bulb 440 abuts a platform to facilitate compression upon contact with a projection 420. In an alternative embodiment (not shown), the bulb 440 may abut a wall of the manual pump 400. In another alternative embodiment (not shown), the bulb does not abut any surfaces.

In addition to the components shown, various gear configurations may be employed to create a mechanical advantage and/or cause the disc 410 and projections 420 to rotate at a rate different from the rate at which the crank 240 is turned.

With continued reference to FIG. 4, the bulb 440 is constructed of rubber, or another pliable, non-porous material. It should be understood, however, that various other materials may be employed. Further, various materials may be used to construct the disc 410 and projections 420. Exemplary materials include polymeric materials and metal materials. In one embodiment, the disc 410 and projections 420 are constructed of substantially the same material. For example, the disc 410 and projections 420 may be one unitary member. In an alternative embodiment, the disc 410 and projections 420 are constructed of different materials.

In operation, the input 210 of the manual intravenous pump 400 is connected to a first fluid line leading to a fluid bag, and the output 220 is connected to a fluid line leading to a subject. In one embodiment, both the input 210 and the output 220 are one-way valves. In one embodiment, when a fluid line is connected to the input 210, fluid immediately begins to flow from the fluid bag, through the fluid line and input 210, and into the internal fluid line 430. In an alternative embodiment, fluid will not begin to flow until the input 210 is opened (e.g., by turning or pressing a valve).

In the illustrated embodiment, once the fluid lines have been connected to the fluid bag, the manual intravenous pump 400, and the subject, and the fluid has begun to flow, an operator may turn the crank 240 of the manual intravenous pump 400 in a counterclockwise direction. As the crank 240 is turned in a counter-clockwise direction, the disc 410 and projections 420 rotate at a corresponding speed and act as a cam on the bulb 440, compressing the bulb 440 and forcing the fluid towards the output 220. Because the projections 420 are spaced apart, spacing allows the bulb 440 to inflate with fluid by negative pressure before the next projection 420 compresses the bulb 440.

It should be understood that, although in the illustrated embodiment a counter-clockwise rotation of the crank 240 is required to force fluid towards the output 220, the components may be re-oriented to require clockwise rotation. In either embodiment, rotation of the crank in a first direction will force fluid to move in a first direction, while rotation of the crank in the opposite direction will force fluid to move in an opposite direction. To prevent the crank from being rotated in an undesired direction, a ratchet and pawl (not shown) or other know stopping mechanism may be employed.

It should be understood that turning the crank 240 at a faster rate may increase the rate at which fluid flows through the output 220 and to a subject, while turning the crank 240 at a slower rate may decrease the rate at which fluid flows through the output 220 and to a subject. The operator may control the speed at which the crank 240 is turned, according to perceived need.

Figure 5:
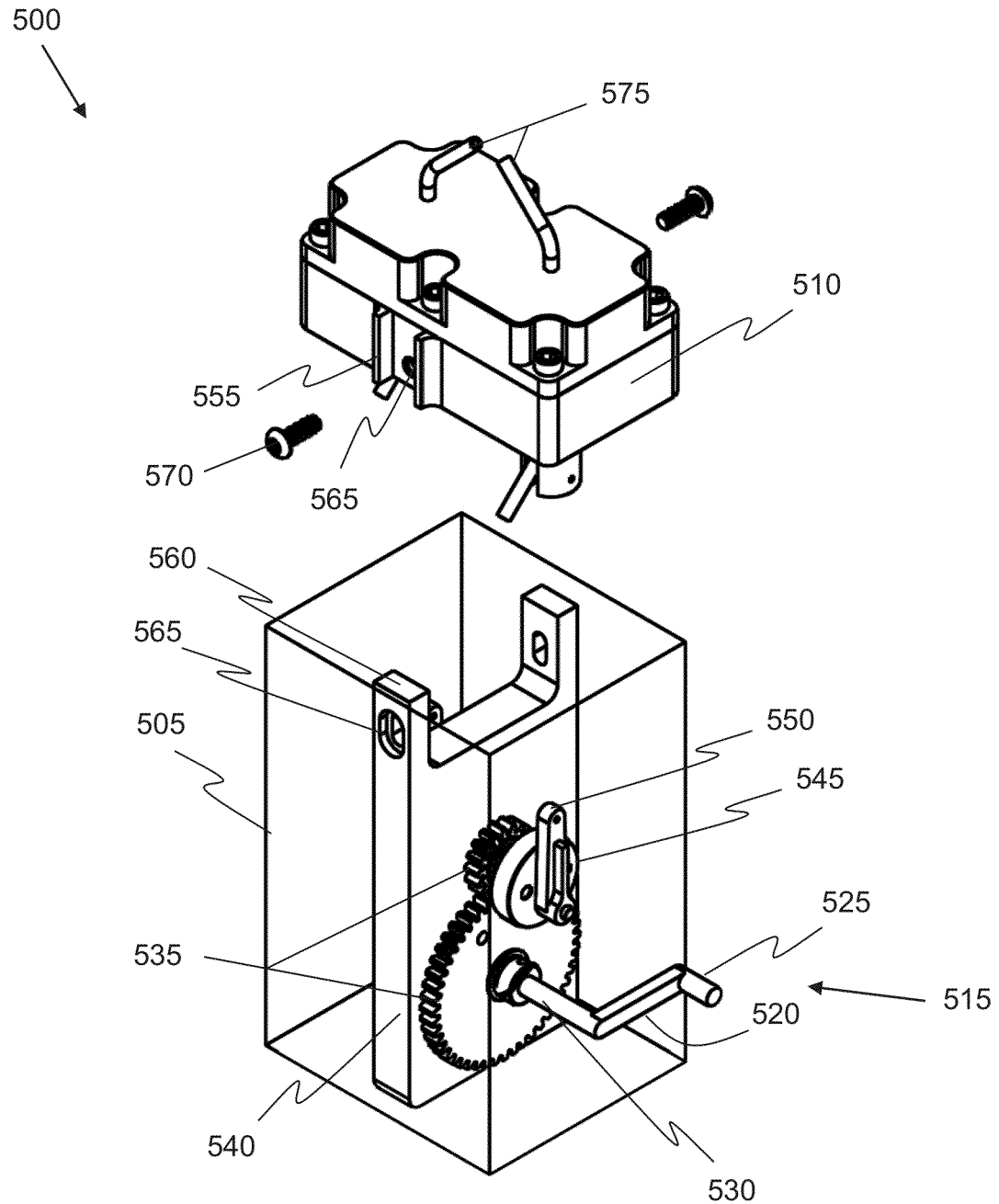
FIG. 5 is an exploded perspective view of an alternative embodiment of a manual intravenous pump having an actuator housing and a reservoir housing.

FIG. 5 illustrates an exploded perspective view of an alternative embodiment of a manual intravenous pump 500 having an actuator housing 505 and at least one reservoir housing 510. The actuator housing 505 includes a manually operable member in the form of a crank 515 having a lever arm 520 and a handle 525. The handle 525 may be fixedly or rotatably connected to the lever arm 520. In an alternative embodiment (not shown), other known manually operable members may be employed in place of a crank.

In the illustrated embodiment, the lever arm 520 is operatively connected to a shaft 530 that turns a series of gears 535 mounted on a base 540. While two gears are shown in the illustrated embodiment, it should be understood that three or more gears may be employed. Alternatively, gears may be omitted.

The series of gears 535 rotates a disc 545 having a plunger 550 pivotally attached thereto. The plunger is one example of a facilitating member configured to facilitate a flow of fluid through a reservoir. The plunger 550 is configured to operatively connect to a pump (not shown) in the reservoir housing 510. The actuator housing 505 may further include a second disc and plunger (not shown) mounted on the opposite side of the base 540 and configured to operatively connect to a second pump (not shown) in the reservoir housing 510.

In the illustrated embodiment, the gears 535 have a fixed gear ratio. In an alternative embodiment (not shown), a gear shift mechanism may be employed to vary the gear ratio. In such an embodiment, an operator may choose to shift gears to increase or decrease the flow of fluid.

The reservoir housing 510 may be configured to be removably attached to the actuator housing 505. In such an embodiment, the reservoir housing 510 may be removed and replaced with a replacement reservoir housing (not shown). For example, the reservoir housing 510 may be replaced after each use for sterility or safety reasons, or to comply with FDA standards, hospital standards, or other standards. In such an embodiment, the reservoir housing 510 may be kept in sterile packaging prior to use. Additionally, the reservoir housing 510 may be filled with fluid prior to packaging, such that no priming is required when a new reservoir housing 510 is attached to the actuator housing 505. In an alternative embodiment (not shown), the reservoir housing may be permanently attached to the actuator housing.

In the illustrated embodiment, the reservoir housing 510 includes a set of rails 555 on opposing sides, configured to slidably receive prongs 560 of the base 540 of the actuator housing 505. The prongs 560 and the sides of the reservoir housing 510 have corresponding apertures 565 configured to receive fasteners 570. In the illustrated embodiment, the fasteners 570 are shown as screws. However, it should be understood that any fasteners may be employed. Exemplary fasteners include bolts, pins, ties, and other known fasteners. In an alternative embodiment (not shown), the apertures and fasteners may be omitted. Instead, the reservoir housing 510 may be attached to the actuator housing 505 by a press fit, a snap fit, clamps, or other attachment means.

The actuator housing 510 includes two input lines (not shown) and two output lines 575. The two input lines may be connected to a single input line (not shown) by a y-connector (not shown). Similarly, the two output lines 575 may be connected to a single output line (not shown) by a y-connector (not shown).

The internal components of two exemplary embodiments of reservoir housings 510 are shown in FIGS. 6A, 6B, 7A, and 7B.

FIGS. 6A and 6B illustrate cross-sections of one embodiment of a reservoir housing 600. The reservoir housing 600 includes two fluid reservoirs defined by a first asymmetric diaphragm pump 610a and a second asymmetric diaphragm pump 610b. The first and second asymmetric diaphragm pumps 610a,b are collapsible bellows or diaphragms that inflate and deflate with fluid. The first asymmetric diaphragm pump 610a is connected to a first piston 620a, a first input line 630a, and a first output line 640b. The second asymmetric diaphragm pump 610b is connected to a second piston 620b, a second input line 630b, and a second output line 640b.

In the illustrated embodiment, the first asymmetric diaphragm pump 610a is out of phase with the second asymmetric diaphragm pump 610b. When the first piston 620a collapses the first asymmetric diaphragm pump 610a, as shown in FIG. 6A, fluid in the first asymmetric diaphragm pump 610a is forced through the first output line 640a. The second piston 620b opens the second asymmetric diaphragm pump 610b concurrently, and fluid flows through the second input line 630b into the second asymmetric diaphragm pump 610b. As the cycle continues, as shown in FIG. 6B, the second piston 620b collapses the second asymmetric diaphragm pump 610b, forcing fluid out of the second diaphragm pump 610b and through the second output line 640b. The first piston 620a opens the first asymmetric diaphragm pump 610a concurrently, and fluid flows through the first input line 630a into the first asymmetric diaphragm pump 610a. Each of the first and second asymmetric diaphragm pumps 610a,b may have check valves (not shown) associated therewith.

In one embodiment, fluid would flow through the asymmetric diaphragm pumps 610a,b and the output lines 640a,b, even when the pumps were not being actuated. In an alternative embodiment, fluid would only flow through the asymmetric diaphragm pumps 610a,b upon actuation. In another alternative embodiment (not shown), the system includes a flow regulation mechanism (i.e., a safety, or an on/off switch) that would allow an operator to prevent fluid from flowing through the output lines 640a,b. Such a flow regulation mechanism may be located on the reservoir housing 600.

In an alternative embodiment (not shown), the first and second asymmetric diaphragm pumps 610a,b may operate in phase. In another alternative embodiment (not shown), the reservoir housing 600 includes a single asymmetric diaphragm pump. In yet another alternative embodiment (not shown), the reservoir housing 600 includes three or more asymmetric diaphragm pumps.

FIGS. 7A and 7B illustrate cross-sections of another embodiment of a reservoir housing 700. The reservoir housing 700 is substantially the same as the reservoir housing 700, except that it includes two fluid reservoirs defined by a first symmetric diaphragm pump 710a and a second symmetric diaphragm pump 710b. The first and second symmetric diaphragm pumps 710a,b are collapsible bellows or diaphragms that inflate and deflate with fluid. The first symmetric diaphragm pump 710a is connected to a first piston 720a, a first input line 730a, and a first output line 740b. The second symmetric diaphragm pump 710b is connected to a second piston 720b, a second input line 730b, and a second output line 740b.

In the illustrated embodiment, the first symmetric diaphragm pump 710a is out of phase with the second symmetric diaphragm pump 710b, and the pumps operate in the same manner as described in FIGS. 7A and 7B. In an alternative embodiment (not shown), the first and second symmetric diaphragm pumps 710a,b may operate in phase. In another alternative embodiment (not shown), the reservoir housing 700 includes a single symmetric diaphragm pump. In yet another alternative embodiment (not shown), the reservoir housing 700 includes three or more symmetric diaphragm pumps.

Figure 8:
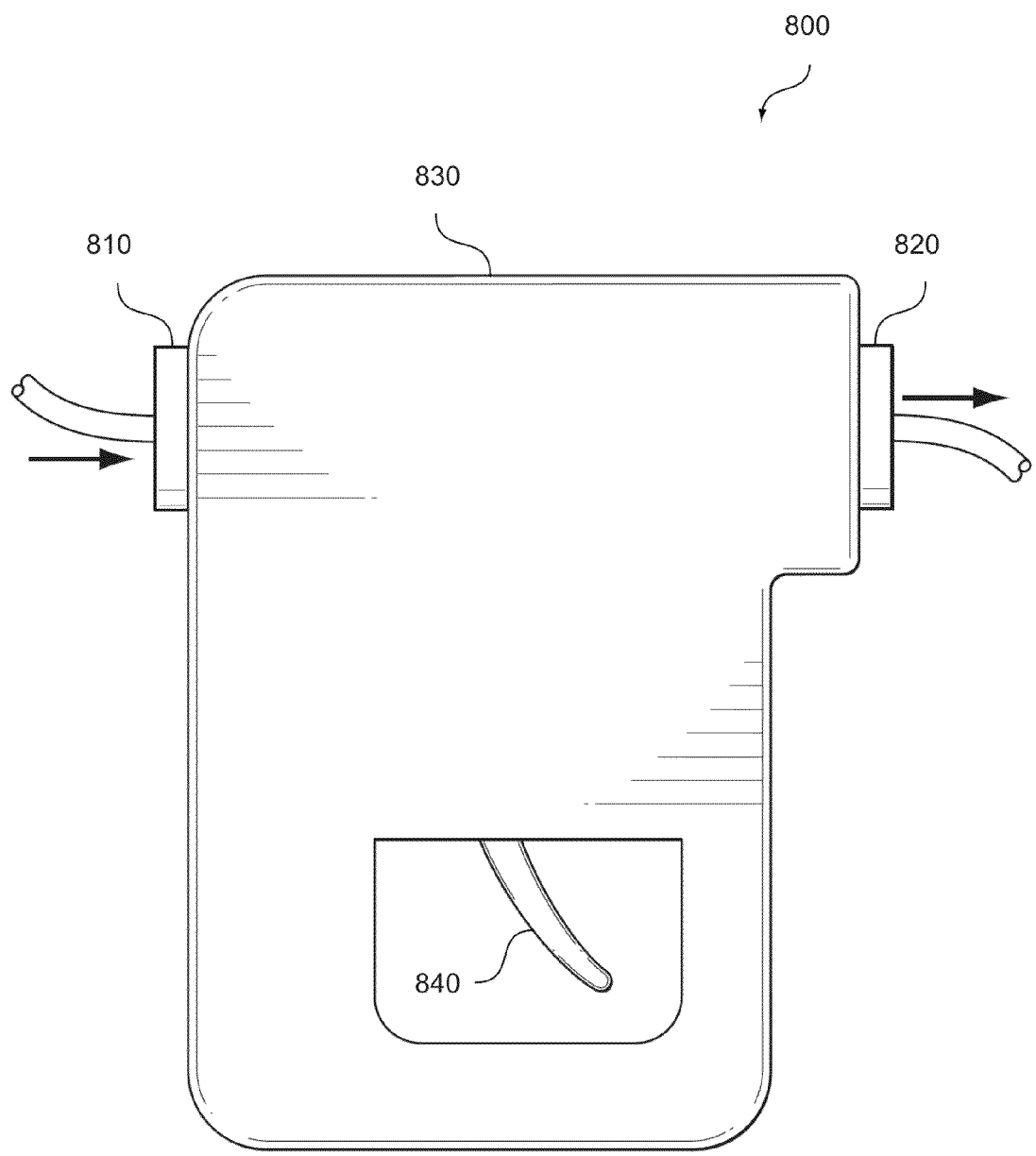
FIG. 8 is a side view of an alternative embodiment of a manual intravenous pump having a trigger.

FIG. 8 illustrates a side view of an alternative embodiment of a manual intravenous pump 800 having an input 810, an output 820, and a body 830. In this embodiment, the manually operable actuator is a trigger 840. This type of manual intravenous pump may be referred to as a "trigger design," "trigger pump," or a "manual piston." The trigger 840 may be configured to pivot or slide transversely with respect to the body 830 of the manual intravenous pump 800. In one embodiment, the trigger 840 is sized to accommodate a single finger of an operator. In an alternative embodiment, the trigger 840 is sized to accommodate two or more fingers of an operator.

With continued reference to FIG. 8, the body 830 of the manual intravenous pump 800 bears resemblance to a pistol. However, it should be understood that this shape is merely exemplary, and any shape may be employed. In one embodiment, the body may have an ergonomic shape.

Although FIG. 8 is described as a side view, it should be understood that the manual intravenous pump 800 may be positioned in multiple orientations, so that the operator may position the device in a comfortable orientation for operation.

The manual intravenous pump 800 may be constructed of various materials. Exemplary materials include polymeric materials and metal materials. Exemplary metal materials include, without limitation, steel, nickel aluminum, copper, iron, and other metals and alloys. Exemplary polymeric materials include, without limitation, EPDM Rubber, polypropylene, polyethylene, and blends of the same. In one embodiment, where the manual intravenous pump is configured for field use (i.e., in an ambulance, or at an accident site), the device may be constructed of materials that are lightweight and durable. Of course, such materials may also be suitable for a device configured for clinical use. In one embodiment, the casing 830 and the trigger 840 are all constructed of substantially the same material. In an alternative embodiment, one or more of these components are constructed of different materials.

Figure 9:
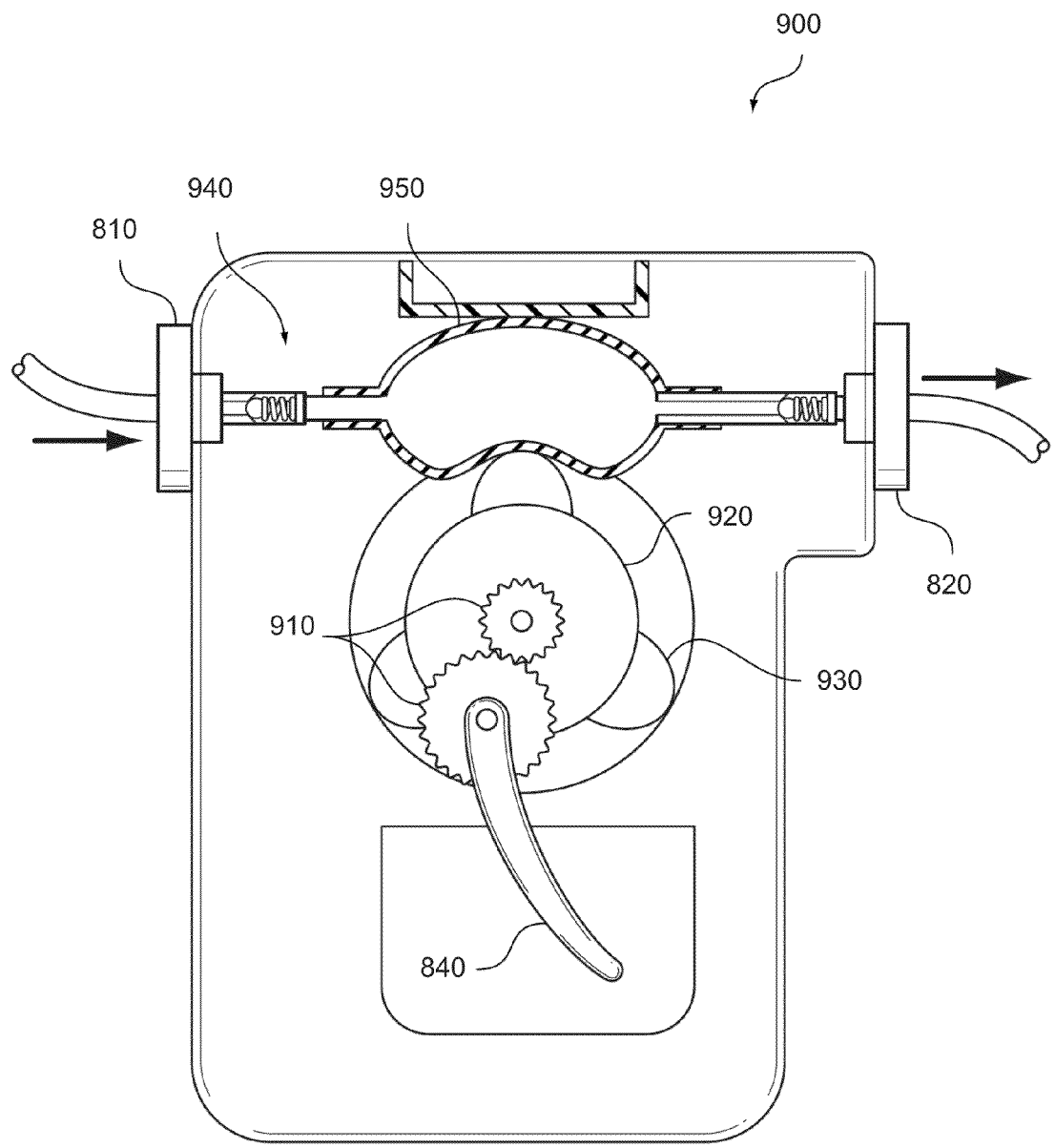
FIG. 9 is a side cutaway view of an alternative embodiment of a manual intravenous pump having a trigger and a bulb.

FIG. 9 is a side view of internal components of one embodiment of a manual intravenous pump 900. The illustrated embodiment is one example of the internal components of the trigger design of a manual intravenous pump 800 shown in FIG. 8.

In the illustrated embodiment, the trigger 840 is pivotally connected to a series of gears 910, which are, in turn, connected to a disc 920 having a plurality of spaced apart, projections 930 extending therefrom. In the illustrated embodiment, two gears are shown. However, it should be understood that any number of gears may be employed. In an alternative embodiment (not shown), no gears are employed, and the trigger is instead directly connected to the disc.

The illustrated manual intravenous pump 900 further includes an internal fluid line 940 having a bulb 950 that defines an internal fluid reservoir. The internal fluid line 940 is in fluid communication with both the input 810 and the output 820 of the manual intravenous pump 900. The disc 920 and projections 930 are positioned adjacent the bulb 950, such that the projections 930 contact and deform the bulb 950 when the disc 920 is rotated. In the illustrated embodiment, the disc 920 includes three projections 930 extending therefrom. However, it should be understood that any number of projections may be employed, including a single projection.

In the illustrated embodiment, the bulb 950 abuts a platform to facilitate compression upon contact with a projection 930. In an alternative embodiment (not shown), the bulb 950 may abut a wall of the manual pump 900. In another alternative embodiment (not shown), the bulb does not abut any surfaces.

With continued reference to FIG. 9, the bulb 950 is constructed of rubber, or another pliable, non-porous material. It should be understood, however, that various other materials may be employed. Further, various materials may be used to construct the disc 920 and projections 930. Exemplary materials include polymeric materials and metal materials. In one embodiment, the disc 920 and projections 930 are constructed of substantially the same material. For example, the disc 920 and projections 930 may be one unitary member. In an alternative embodiment, the disc 920 and projections 930 are constructed of different materials.

In operation, the input 810 of the manual intravenous pump 900 is connected to a first fluid line leading to a fluid bag, and the output 820 is connected to a fluid line leading to a subject. In one embodiment, both the input 810 and the output 820 are one-way valves. In one embodiment, when a fluid line is connected to the input 810, fluid immediately begins to flow from the fluid bag, through the fluid line and input 810, and into the internal fluid line 940. In an alternative embodiment, fluid will not begin to flow until the input 810 is opened (e.g., by turning or pressing a valve).

In the illustrated embodiment, once the fluid lines have been connected to the fluid bag, the manual intravenous pump 900, and the subject, and the fluid has begun to flow, an operator may squeeze the trigger 840 of the manual intravenous pump 900. As the trigger 840 is squeezed, gears 910 cause the disc 920 and projections 930 to rotate and act as a cam on the bulb 950, compressing the bulb 950 and forcing the fluid towards the output 820. Because the projections 930 are spaced apart, spacing allows the bulb 950 to inflate with fluid by negative pressure before the next projection 930 compresses the bulb 950. When the trigger 840 is released, a ratcheting mechanism (not shown) or other such mechanism may be employed to prevent the disc 920 and projections 930 from moving in the reverse direction.

It should be understood that squeezing the trigger 840 at a faster rate may increase the rate at which fluid flows through the output 820 and to a subject, while squeezing the trigger 840 at a slower rate may decrease the rate at which fluid flows through the output 820 and to a subject. The operator may control the speed at which the trigger 840 is squeezed, according to perceived need.

Figure 10:
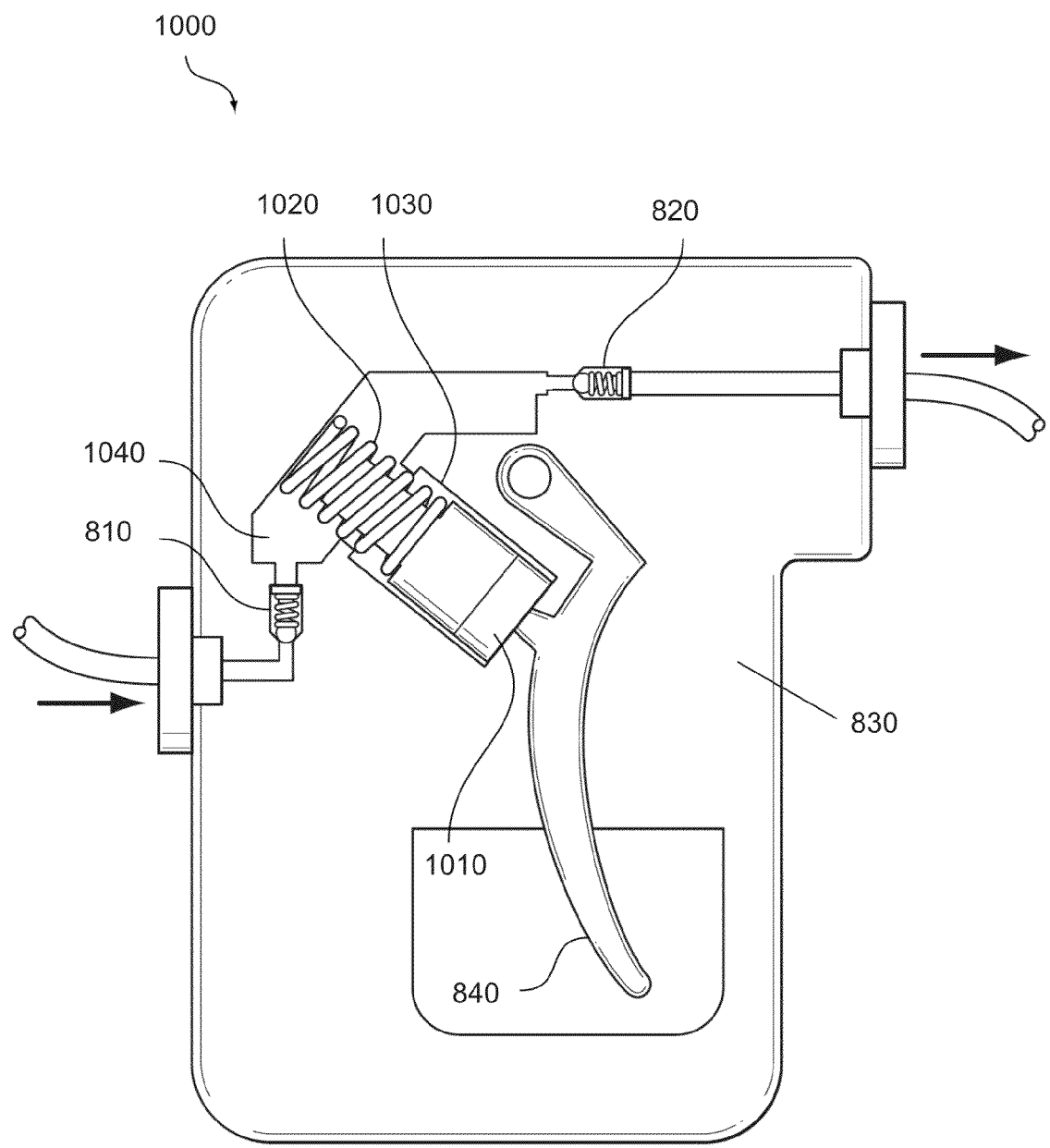
FIG. 10 is a side cutaway view of another alternative embodiment of a manual intravenous pump having a trigger and a piston.

FIG. 10 is a cutaway side view of internal components of one embodiment of a manual intravenous pump 700. The illustrated embodiment is one example of the internal components of the trigger design of a manual intravenous pump 800 shown in FIG. 8.

In the illustrated embodiment, the trigger 840 is pivotally connected to the casing 830 and is further connected to a piston 1010. The piston 1010 is biased towards the trigger 840 by a biasing mechanism 1020. In the illustrated embodiment, the biasing mechanism 1020 is shown as a spring. However, it should be understood that any known biasing mechanism may be employed. The piston 1010 and biasing mechanism 1020 are housed in a cylinder 1030 that is part of a larger fluid reservoir 1040. The fluid reservoir is connected to the input 810 and output 820. In the illustrated embodiment, both the input 810 and output 820 are one-way valves.

In operation, an operator squeezes the trigger 840, which pushes the piston 1020 into the cylinder 1030, compressing the biasing mechanism 1020. When the piston 1020 is pushed into the cylinder 1030, the volume of the fluid reservoir 1040 is reduced, forcing fluid through the output 820. When the trigger is released, the biasing mechanism 1020 pushes the piston 1020 back out of the cylinder, expanding the volume of the fluid reservoir 1040 and drawing more fluid in through the input 810. The one way valves of the input 810 and output 820 prevent the fluid from flowing in an undesired direction.

Figure 11:
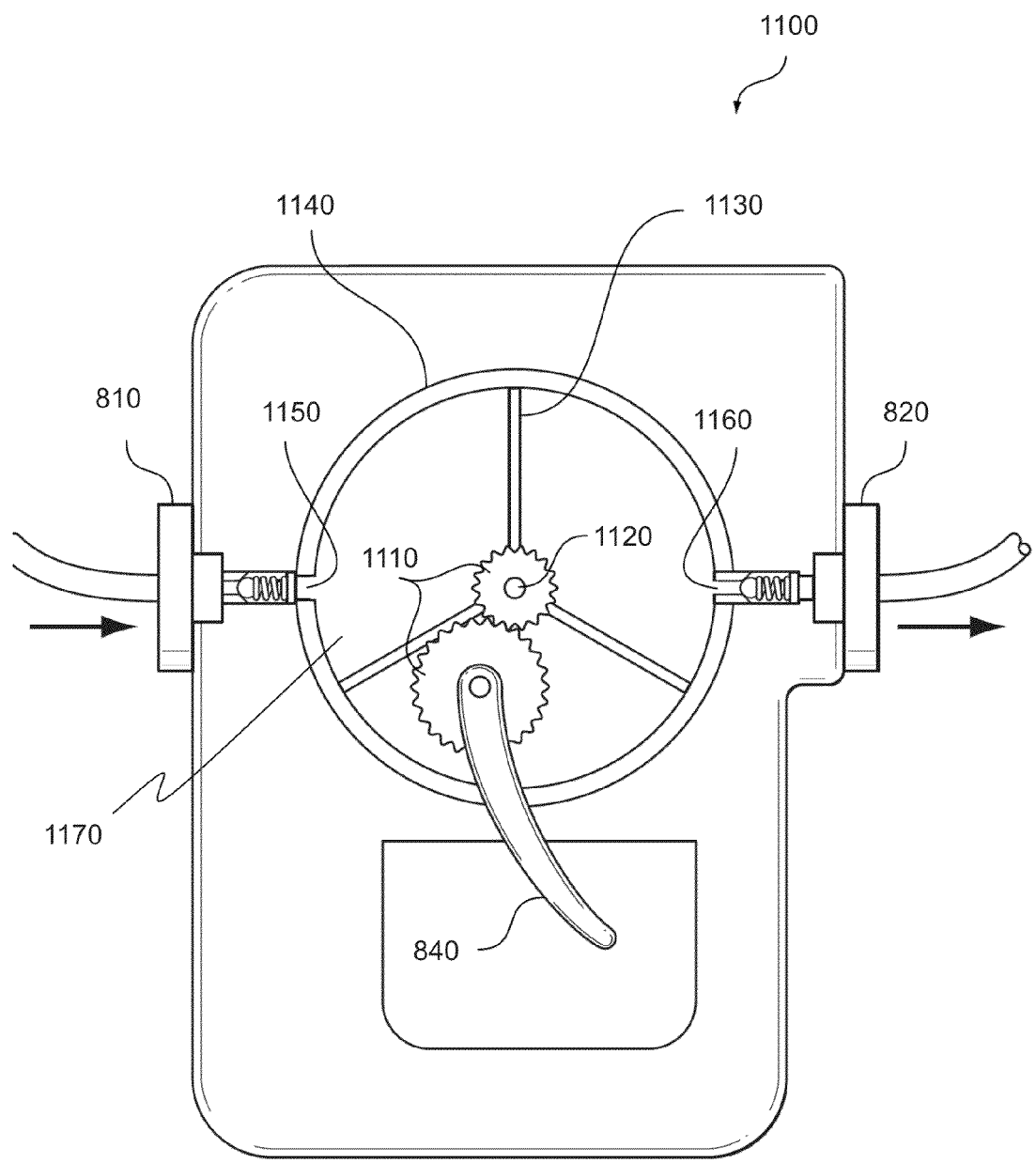
FIG. 11 is a side cutaway view of another alternative embodiment of a manual intravenous pump having a trigger and rotary chambers.

FIG. 11 is a side cutaway view of one embodiment of a manual intravenous pump 1100. The illustrated embodiment is another example of the internal components of the trigger design of a manual intravenous pump 800 shown in FIG. 8.

In the illustrated embodiment, the trigger 840 is connected to a series of gears 1110, which are connected rod 1120 having a plurality of partitions 1130 extending therefrom. While two gears 1110 are illustrated, it should be understood that three or more gears may be employed. Alternative, the trigger 840 may be directly connected to the rod 1120 without the use of intervening gears.

With continued reference to FIG. 11, the rod 1120 and partitions 1130 are positioned inside a cylinder 1140 that defines an internal fluid reservoir. The cylinder 1140 has a first opening 1150 in fluid communication with the input 810 of the manual intravenous pump 1100 and a second opening 1160 in fluid communication with the output 820 of the manual intravenous pump 1100. The rod 1120 and partitions 1130 form a plurality of rotary chambers 1170 in the cylinder 1140. In the illustrated embodiment, the rod 1120 includes three partitions 1130 extending therefrom, which form three rotary chambers 1170 in the cylinder 1140. However, it should be understood that any number of partitions may be employed, including a single partition.

In addition to the components shown, various gear configurations may be employed to create a mechanical advantage and/or cause the rod 1120 and partitions 1130 to rotate at a rate different from the rate at which the trigger 840 is squeezed.

With continued reference to FIG. 11, the partitions 1130 extend from the rod 1120 to an inner surface of the cylinder 1140. In one embodiment, at least the ends of the partitions are constructed of rubber, or another pliable, non-porous material, to form a seal. It should be understood, however, that various other materials may be employed. In an alternative embodiment, the partitions 1130 do not extend to the inner surface of the cylinder 1140.

Various materials may be used to construct the rod 1120, partitions 1130, and cylinder 1140. Exemplary materials include polymeric materials and metal materials. In one embodiment, the rod 1120, partitions 1130, and cylinder 1140 are constructed of polymeric materials that resist corrosion after prolonged exposure to saline solutions and other commonly used intravenous fluids. In one embodiment, the rod 1120, partitions 1130, and cylinder 1140 are all constructed of substantially the same material. In an alternative embodiment, one or more of these components are constructed of different materials.

In operation, the input 810 of the manual intravenous pump 1100 is connected to a first fluid line leading to a fluid bag, and the output 820 is connected to a fluid line leading to a subject. In one embodiment, both the input 810 and the output 820 are one-way valves. In one embodiment, when a fluid line is connected to the input 810, fluid immediately begins to flow from the fluid bag, through the fluid line and input 810, and into the first of the plurality of chambers 1170. In an alternative embodiment, fluid will not begin to flow until the input 810 is opened (e.g., by turning or pressing a valve).

Once the fluid lines have been connected to the fluid bag, the manual intravenous pump 1100, and the subject, and the fluid has begun to flow, an operator may squeeze the trigger 840 of the manual intravenous pump 1100. As the trigger 840 is squeezed, the partitions 1130 rotate at a corresponding speed and force the fluid from the first opening 1150 of the cylinder 1140 towards the second opening 1160. Squeezing the trigger 840 at a faster rate may increase the rate at which fluid flows through the output 820 and to a subject, while squeezing the trigger 840 at a slower rate may decrease the rate at which fluid flows through the output 820 and to a subject. The operator may control the speed at which the trigger 840 is squeezed, according to perceived need.

Figure 12:
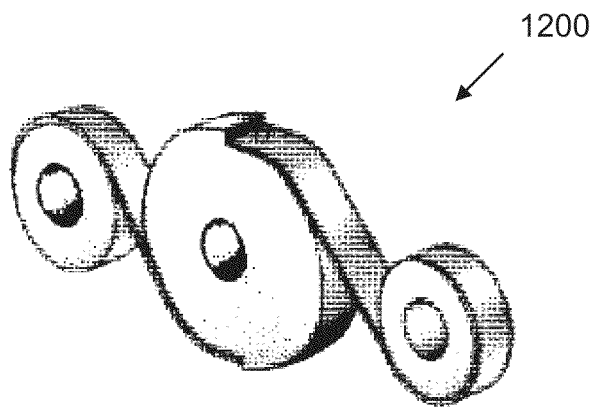
FIG. 12 is a perspective view of an exemplary twin spring motor for use in a manual intravenous pump having a trigger.
Figure 13:
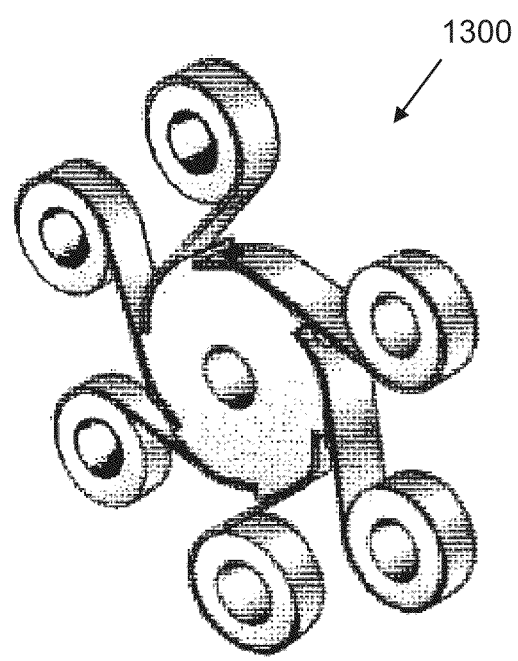
FIG. 13 is a perspective view of an exemplary sextupled spring motor for use in a manual intravenous pump having a trigger.

In another alternative embodiment, the trigger pump may employ one or more spring motors to facilitate pumping. For example, FIG. 12 illustrates a perspective view of an exemplary twin spring motor 1200 which may be employed in a trigger pump. As another example, FIG. 13 illustrates a perspective view of an exemplary sextupled spring motor 1300 which may be employed in a trigger pump. In either example, the spring motor may be configured to coil and store energy when a trigger is depressed. When the trigger is released, the spring motor releases energy to compress a pump. In yet another embodiment, an electric motor may be employed to actuate the pumps.

In still another alternative embodiment (not shown), the trigger pump employs a separate reservoir housing, such as the reservoir housing 505 shown in FIG. 5, reservoir housing 600 shown in FIGS. 6A,B, or reservoir housing 700 shown in FIGS. 7A,B. Such a reservoir housing may be removably attached to the device, such that the reservoir housing may be removed and replaced as desired.

Figure 14:
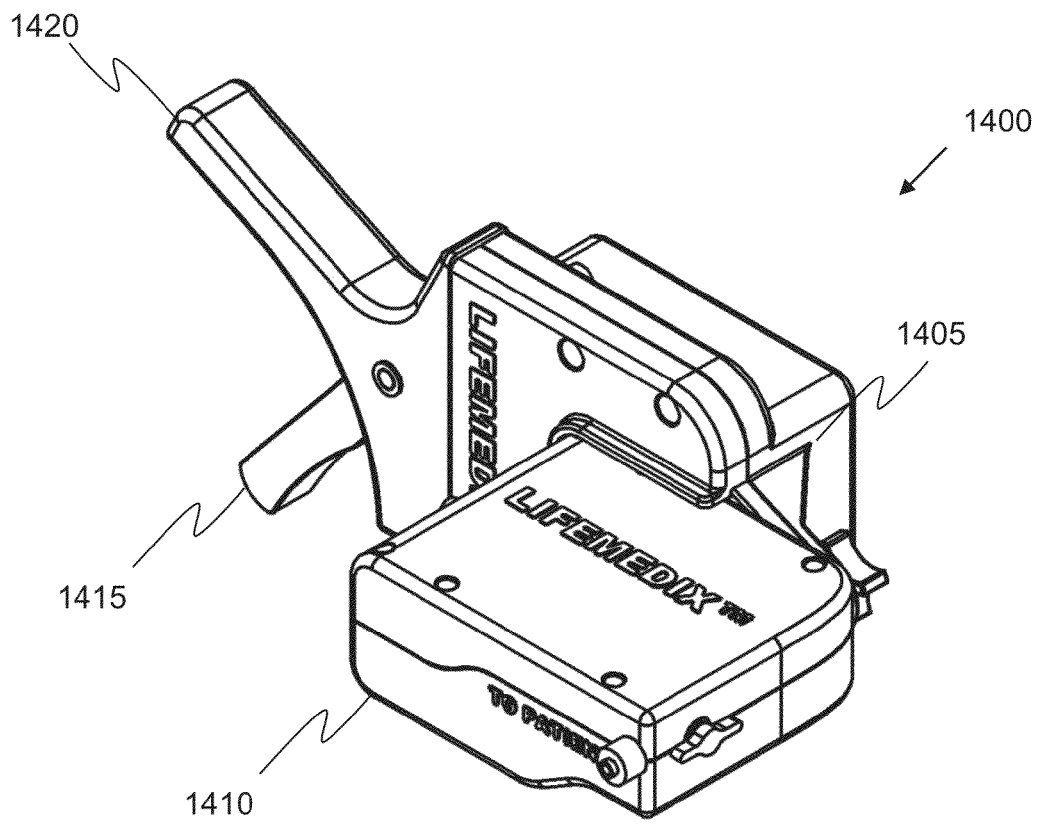
FIG. 14 is a perspective view of another alternative embodiment of a manual intravenous pump having at least one pivoting handle.
Figure 15:
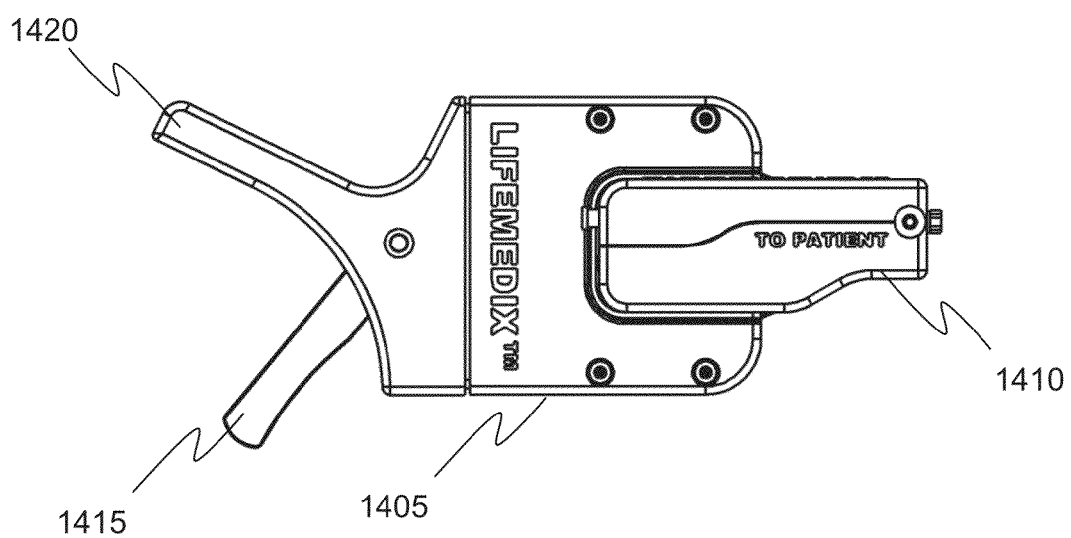
FIG. 15 is a side view of the manual intravenous pump having at least one pivoting handle.

FIGS. 14 and 15 illustrate a perspective view and side view, respectively, of another alternative embodiment of a manual intravenous pump 1400 having an actuator housing 1405 and at least one reservoir housing 1410. The actuator housing 1405 includes a manually operable member in the form of a pivotal handle 1415 that is pivotally connected to a stationary handle 1420. Accordingly, this type of manual intravenous pump may be referred to as a "pivoting handle design" or "pivoting handled pump." In this embodiment, the pump is actuated by pivoting the pivotal handle 1415 towards the stationary handle 1420. In an alternative embodiment (not shown), the actuator housing may include two pivotal handles.

The reservoir housing 1410 may be configured to be removably attached to the actuator housing 1405. In such an embodiment, the reservoir housing 1410 may be removed and replaced with a replacement reservoir housing (not shown). For example, the reservoir housing 1410 may be replaced after each use for sterility or safety reasons, or to comply with FDA standards, hospital standards, or other standards. In such an embodiment, the reservoir housing 1410 may be kept in sterile packaging prior to use. Additionally, the reservoir housing 1410 may be filled with fluid prior to packaging, such that no priming is required when a new reservoir housing 1410 is attached to the actuator housing 1405. In an alternative embodiment (not shown), the reservoir housing may be permanently attached to the actuator housing.

Figure 16:
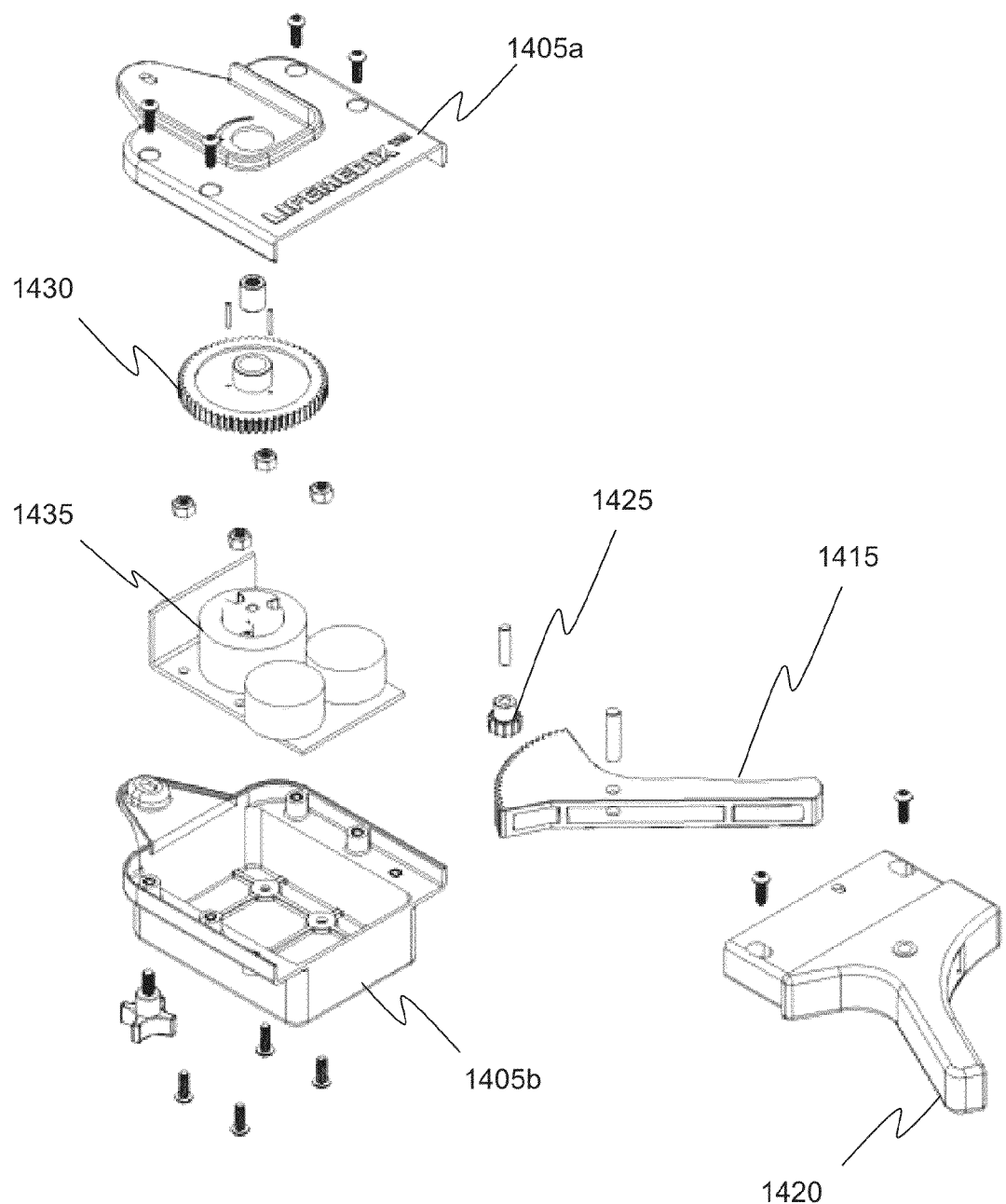
FIG. 16 is an exploded perspective view of an actuator housing of the manual intravenous pump having at least one pivoting handle.

FIG. 16 illustrates an exploded perspective view of the actuator housing 1405 pivoting handled pump 1400. In the illustrated embodiment, the actuator housing includes a first actuator housing 1405a that is fastened to a second actuator housing 1405b by a plurality of fasteners. In addition to housing the pivotal handle 1415 and the stationary handle 1420, the actuator housing additionally houses a first gear 1425 having teeth configured to engage corresponding teeth of the pivotal handle 1415. The teeth of the first gear 1425 are further configured to engage teeth of a second gear 1430, which rotates about an axis of a spring loaded gear box 1435. The spring loaded gear box 1435 is configured to store and release energy, using springs such as those shown in FIGS. 12 and 13. While the illustrated embodiment shows two gears 1425, 1430, it should be understood that a single gear may be employed. In an alternative embodiment (not shown), three or more gears may be employed.

Figure 17:
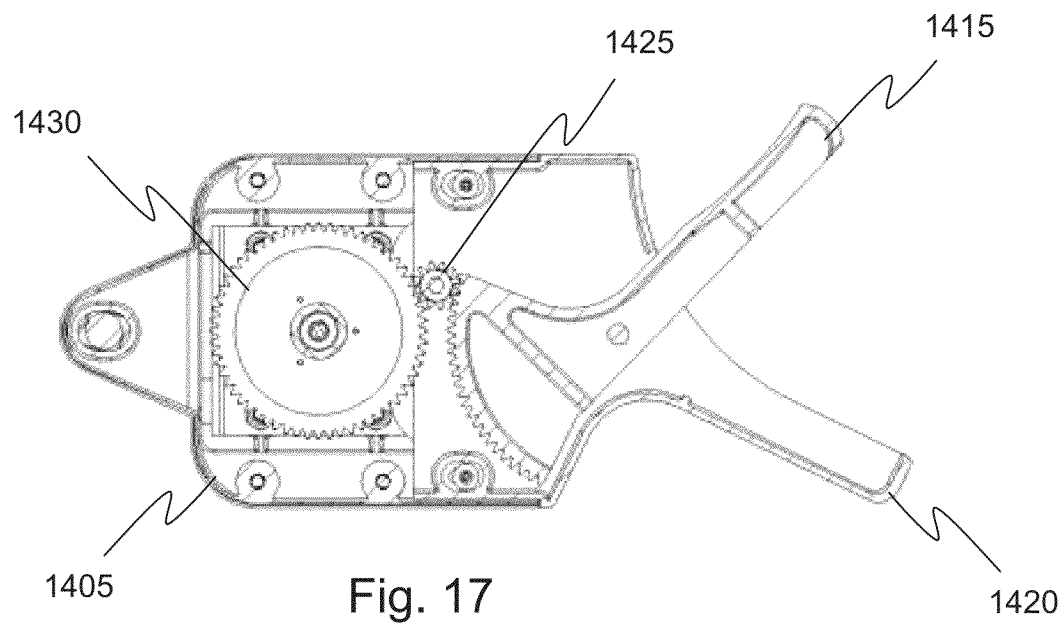
FIG. 17 is a cross section of the actuator housing of the manual intravenous pump having at least one pivoting handle.

FIG. 17 illustrates a cross-section of the actuator housing 1405, and further shows the pivotal handle 1415 engaging the first gear 1425, which, in turn, engages the second gear 1430. The pivotal handle 1415 is connected to a biasing member, such as a spring, that biases the pivotal handle 1415 away from the stationary handle 1420. In one embodiment, the pivotal handle 1415 is configured such that its teeth engage the teeth of the first gear 1425 when the pivotal handle 1415 is pivoted towards the stationary handle 1420, but the teeth disengage when the pivotal handle 1415 pivots away from the stationary handle 1420. In this embodiment, a large amount of energy may be stored at one time, which may then be released by the spring loaded gear box. In an alternative embodiment, the teeth of the pivotal handle 1415 remain engaged with the teeth of the first gear 1425 when the pivotal handle pivots away from the stationary handle 1420.

Figure 18:
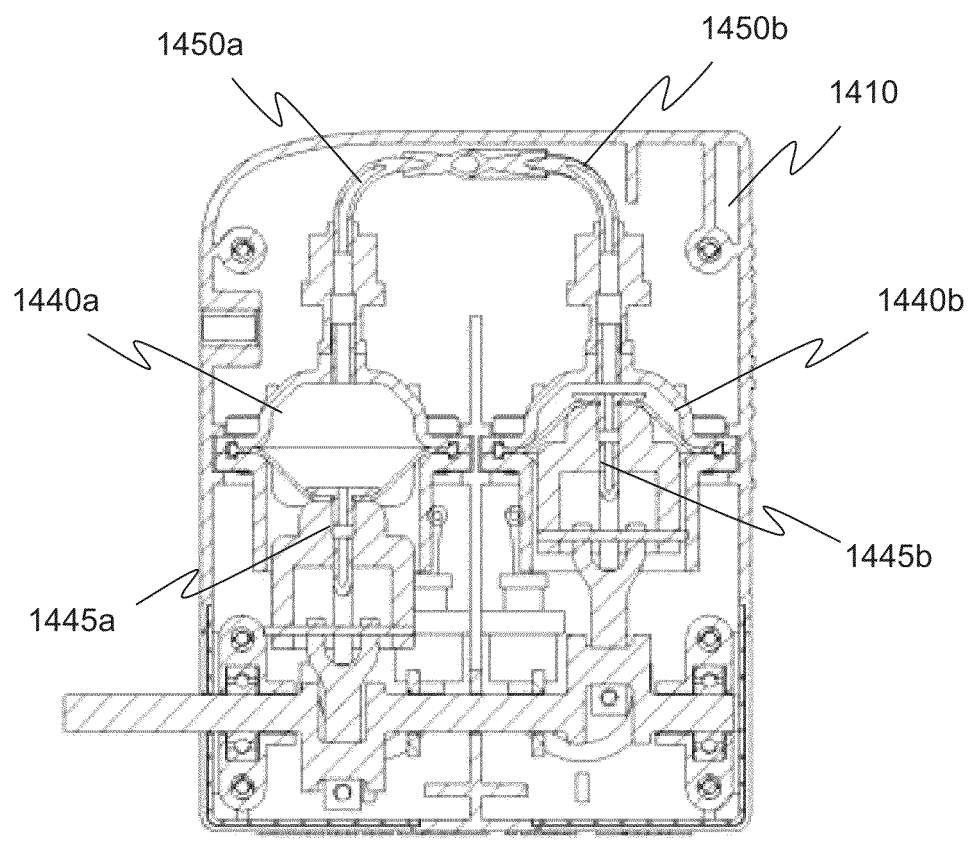
FIG. 18 is a cross section of a reservoir housing for a manual intravenous pump.

FIG. 18 illustrates a cross section of the reservoir housing 1410. In the illustrated embodiment, the reservoir housing has substantially the same components as the reservoir housing 700, including first and second symmetric diaphragm pumps 1440a,b connected to first and second input lines 1445a,b and first and second output lines 1450a,b. In the illustrated embodiment, the first and second symmetric diaphragm pumps 1440a,b operate out of phase with respect to each other. In an alternative embodiment (not shown), the first and second symmetric diaphragm pumps 1440a,b operate in phase with respect to each other. In another alternative embodiment (not shown), asymmetric diaphragm pumps may be employed.

Figure 19:
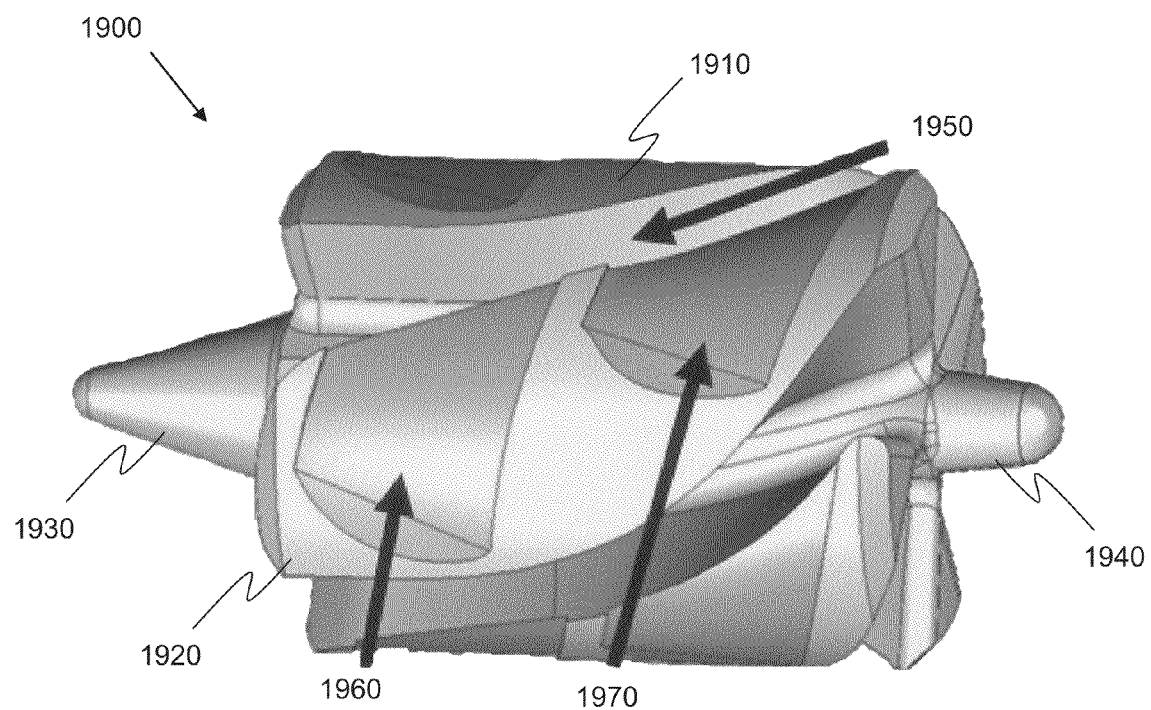
FIG. 19 is a cut away view of an alternative embodiment of a pump for use in a manual intravenous pump.

FIG. 19 illustrates a cut away view of an alternative embodiment of a pump 1900 for use in a manual intravenous pump. The pump 1900 is an axial flow pump having an outer housing 1910 and a bladed rotor 1920, and may be employed with any embodiment of a manual intravenous pump described herein. The pump 1900 may be employed as a single pump, or in combination with one more additional pumps.

In the illustrated embodiment, the outer housing 1910 has a first a projection 1930 along a first axis and the rotor has a second projection 1940. The second projection 1940 may be located on the first axis, or it may be located along a second axis different from the first axis. The bladed rotor 1920 is disposed in the outer housing 1910 in a manner providing clearance between an outer surface of the bladed rotor 1920 and an inner surface of the outer housing 1910. This clearance defines one or more flow channels 1950 for a fluid.

The bladed rotor 1920 further includes at least one hydrodynamic bearing. In the illustrated embodiment, the rotor includes a first hydrodynamic bearing 1960 and a second hydrodynamic bearing 1970. The first and second hydrodynamic bearings 1960, 1970 are larger and wider than the area between blades where fluid flows. In an alternative embodiment (not shown), the first and second hydrodynamic bearings 1960, 1970 are narrower than the area between blades where fluid flows.

Figure 20:
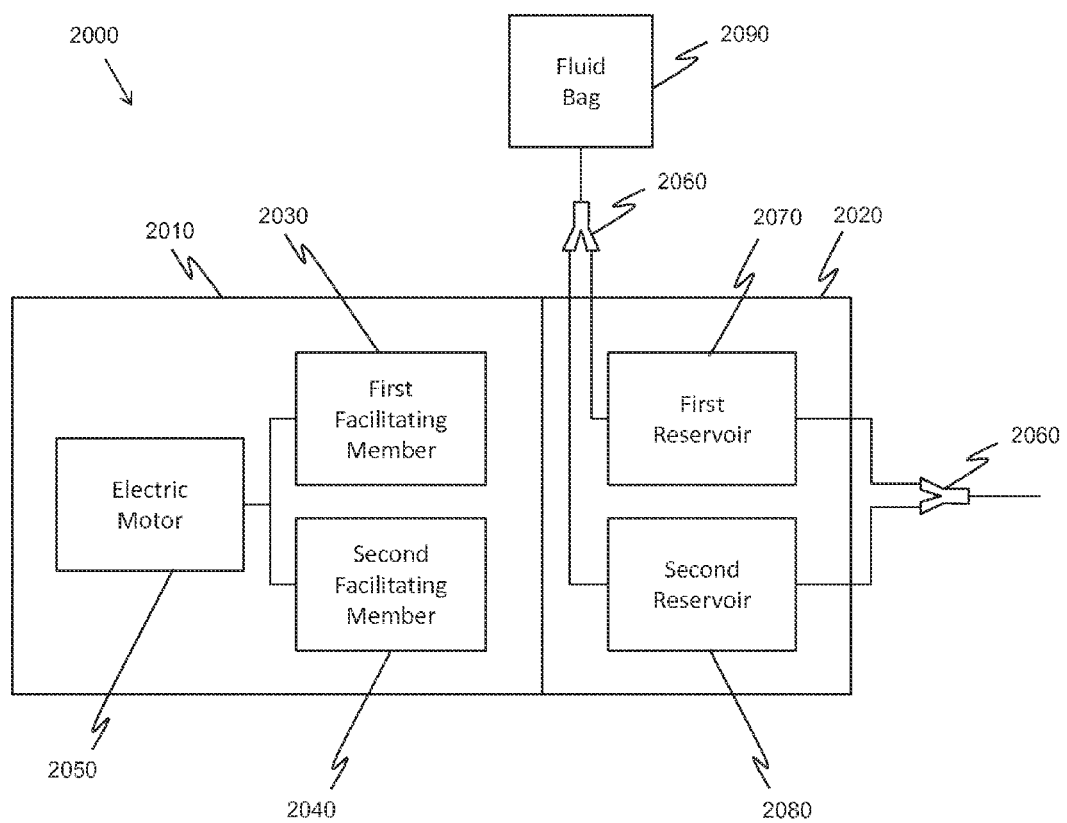
FIG. 20 is a schematic drawing showing an alternative embodiment of an intravenous pump.

FIG. 20 illustrates a schematic drawing showing an alternative embodiment of an intravenous pump 2000. The intravenous pump 2000 includes an actuator housing 2010 and a reservoir housing 2020. The actuator housing 2010 includes a first facilitating member 2030 and a second facilitating member 2040. An electric motor 2050 is configured to actuate the first facilitating member 2030 and the second facilitating member 2040.

The reservoir housing 2020 is removably attached to the actuator housing 2010 and includes a first fluid input line and a second fluid input line. The first fluid input line has a first end and a second end, with the first end connected to a y-connector 2060 and a second end connected to a first fluid reservoir 2070. The second fluid input line has a first end and a second end, with the first end connected to the y-connector 2060 and a second end connected to a second fluid reservoir 2080. The y-connector 2060 connects the first fluid input line and the second fluid input line to a single input line operatively connected to a fluid bag 2090 that is external to the actuator housing 2010 and external to the reservoir housing 2020. A fluid output line is connected to the first fluid reservoir 2070 and the second fluid reservoir 2080 through a y-connector 2060.

The first facilitating member 2030 is configured to facilitate flow of a fluid from the fluid bag 2090 through the first fluid reservoir 2070. The second facilitating member 2040 is configured to facilitate flow of the fluid from the fluid bag 2090 through the second fluid reservoir 2080. The first end of the first fluid input line and the first end of the second fluid input line each remain operatively connected to the fluid bag 2090 during actuation of the first facilitating member 2030 and the second facilitating member 2040.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

What is claimed is:

1. An intravenous pump comprising:
an actuator housing including a first facilitating member and a second facilitating member; and
a reservoir housing removably attached to the actuator housing, wherein the reservoir housing includes:
a first fluid input line, having a first end and a second end, wherein the first end is directly connected to a y-connector,
a first fluid reservoir operatively connected to the second end of the first fluid input line,
a second fluid input line, having a first end and a second end, wherein the first end is directly connected to the y-connector, wherein the y-connector connects the first fluid input line and the second fluid input line to a single input line configured to be operatively connected to a fluid bag that is external to the actuator housing and external to the reservoir housing,
a second fluid reservoir operatively connected to the second end of the second fluid input line, and
at least one fluid output line operatively connected to the first fluid reservoir and the second fluid reservoir,
wherein the first facilitating member is configured to facilitate flow of a fluid from the fluid bag through the first fluid reservoir,
wherein the second facilitating member is configured to facilitate flow of the fluid from the fluid bag through the second fluid reservoir, and
wherein the first end of the first fluid input line and the first end of the second fluid input line each remain operatively connected to the fluid bag during actuation of the first facilitating member and the second facilitating member.

2. The intravenous pump of claim 1, wherein the first facilitating member is configured to operate out of phase with the second facilitating member.

3. The intravenous pump of claim 1, wherein the first facilitating member is configured to operate in phase with the second facilitating member.

4. The intravenous pump of claim 1, wherein each of the first and second fluid reservoirs is an asymmetric diaphragm pump.

5. The intravenous pump of claim 1, wherein each of the first and second fluid reservoirs is a symmetric diaphragm pump.

6. The intravenous pump of claim 1, further comprising a manually operable member configured to actuate the first facilitating member and the second facilitating member.

7. The intravenous pump of claim 1, further comprising an electric motor configured to actuate the first facilitating member and the second facilitating member.

8. A device comprising:
at least one housing;
a first input line operatively connected to a fluid bag that is external to the at least one housing;
a second input line operatively connected to the fluid bag;
a first fluid reservoir operatively connected to the first input line;
a second fluid reservoir operatively connected to the second input line;
a y-connector connected to the fluid bag via a single input line, wherein the y-connector is directly connected to the first input line and is directly connected to the second input line;
an output line operatively connected to the first fluid reservoir and the second fluid reservoir; and
an actuator, configured to facilitate a flow of fluid from the fluid bag, through the first input line and second input line, and through the first fluid reservoir and second fluid reservoir, wherein each of the first and second input lines remains operatively connected to the fluid bag during operation of the actuator.

9. The device of claim 8, wherein the actuator is a manually operable actuator.

10. The device of claim 8, wherein the actuator is an electric motor.

11. The device of claim 8, wherein the at least one housing includes a reservoir housing configured to house the first and second fluid reservoirs.

12. The device of claim 11, wherein the at least one housing further includes an actuator housing configured to house the actuator, wherein the reservoir housing is removably attached to the actuator housing.

13. The device of claim 8, wherein each of the first and second fluid reservoirs is a diaphragm pump.

14. The device of claim 8, wherein each of the first and second fluid reservoirs is defined by a cylinder.

15. An intravenous fluid pumping kit comprising:
a fluid bag;
a y-connector connected to the fluid bag via a single input line;
a first fluid input line directly connected to the y-connector;
a second fluid input line directly connected to the y-connector;
a fluid output line; and
a pump including:
a housing;
a first fluid reservoir connected to the first fluid input line, the first fluid reservoir being further connected to the fluid output line;
a second fluid reservoir connected to the second fluid input line, the second fluid reservoir being further connected to the fluid output line; and
a facilitator configured to facilitate flow of fluid through the first and second fluid reservoirs from the fluid bag, through the first and second fluid inputs, and to the fluid output,
wherein the fluid bag is external to the housing.

16. The intravenous fluid pumping kit of claim 15, wherein the pump housing includes a first housing and a second housing.

* * * * *